US009801265B2

(12) United States Patent
Bullock et al.

(10) Patent No.: US 9,801,265 B2
(45) Date of Patent: Oct. 24, 2017

(54) HIGH DYNAMIC RANGE MEASUREMENT SYSTEM FOR PROCESS MONITORING

(71) Applicant: Verity Instruments, Inc., Carrollton, TX (US)

(72) Inventors: Larry Arlos Bullock, Carrollton, TX (US); John D. Corless, Carrollton, TX (US); Mark Anthony Meloni, Carrollton, TX (US); Mike Whelan, Carrollton, TX (US)

(73) Assignee: Verity Instruments, Inc., Carrollton, TX (US)

( * ) Notice: Subject to any disclaimer, the term of this patent is extended or adjusted under 35 U.S.C. 154(b) by 0 days.

(21) Appl. No.: 15/045,766

(22) Filed: Feb. 17, 2016

(65) Prior Publication Data

US 2016/0316546 A1    Oct. 27, 2016

Related U.S. Application Data

(63) Continuation of application No. 14/696,370, filed on Apr. 24, 2015, now Pat. No. 9,310,250.

(51) Int. Cl.
| | |
|---|---|
| G01J 3/28 | (2006.01) |
| H05B 41/30 | (2006.01) |
| G01J 3/26 | (2006.01) |
| G01J 3/10 | (2006.01) |
| G01J 3/02 | (2006.01) |
| G01N 21/84 | (2006.01) |
| G01J 3/12 | (2006.01) |

(52) U.S. Cl.
CPC ............ *H05B 41/30* (2013.01); *G01J 3/0205* (2013.01); *G01J 3/027* (2013.01); *G01J 3/10* (2013.01); *G01J 3/26* (2013.01); *G01N 21/84* (2013.01); *G01J 2003/1278* (2013.01); *G01N 2201/061* (2013.01); *G01N 2201/0696* (2013.01)

(58) Field of Classification Search
CPC ...... G01J 1/0407; G01J 1/0411; G01J 1/0437; G01J 1/4228; G01J 1/4257; H01S 3/09415; H01S 3/0014
USPC ....................................................... 356/326
See application file for complete search history.

(56) References Cited

U.S. PATENT DOCUMENTS

| | | | |
|---|---|---|---|
| 3,780,344 A | 12/1973 | Paget | |
| 3,978,465 A | 8/1976 | Goode | |

(Continued)

FOREIGN PATENT DOCUMENTS

| | | | |
|---|---|---|---|
| JP | 2008288480 A | 11/2008 | |
| JP | 2008304407 A | 12/2008 | |

(Continued)

OTHER PUBLICATIONS

JP Office Action for Application No. JP2016-059091; Mailing No. 232350; dated May 29, 2017; (English translation and original) 5 pgs.

*Primary Examiner* — Tarifur Chowdhury
*Assistant Examiner* — Md M Rahman

(57) ABSTRACT

A digital flashlamp controller, a flashlamp control system and a method of controlling a flashlamp bulb employing digital control electronics are provided herein. In one embodiment, the digital flashlamp controller includes: (1) a trigger interface configured to provide firing signals to control a trigger element for a flashlamp bulb and (2) digital electronics configured to generate the firing signals and control multiple pulsing of the flashlamp bulb.

17 Claims, 13 Drawing Sheets

(56) References Cited

U.S. PATENT DOCUMENTS

| | | |
|---|---|---|
| 3,993,917 A | 11/1976 | Kalter |
| 4,270,079 A | 5/1981 | Ikawa |
| 5,034,662 A | 7/1991 | Nishida et al. |
| 5,255,277 A * | 10/1993 | Carvalho ............. H05B 41/325 315/208 |
| 5,432,410 A | 7/1995 | Yamada et al. |
| 5,476,044 A | 12/1995 | Boucher |
| 6,456,511 B1 | 9/2002 | Wong |
| 7,239,194 B2 | 7/2007 | Azrai et al. |
| 8,374,012 B2 | 2/2013 | Raptis et al. |
| 8,451,628 B2 | 5/2013 | Strzalkowski |
| 8,896,315 B1 | 11/2014 | Davies |
| 9,209,653 B2 | 12/2015 | Maynard et al. |
| 2004/0189142 A1 | 9/2004 | Knieser et al. |
| 2005/0213267 A1 | 9/2005 | Azrai et al. |
| 2008/0067946 A1 | 3/2008 | Simonsen et al. |
| 2008/0080864 A1 | 4/2008 | Bai |
| 2008/0180414 A1* | 7/2008 | Fung ................... G09G 3/3426 345/204 |
| 2008/0290810 A1* | 11/2008 | Kiernan ................ H05B 41/34 315/224 |
| 2011/0145194 A1 | 6/2011 | Figus et al. |
| 2012/0326054 A1* | 12/2012 | Meloni .............. G01N 21/6489 250/459.1 |
| 2013/0016343 A1 | 1/2013 | Corless et al. |
| 2013/0093400 A1 | 4/2013 | Maynard et al. |
| 2013/0094853 A1 | 4/2013 | Mizutani et al. |
| 2013/0257446 A1* | 10/2013 | Soell ................... B60L 11/1803 324/503 |
| 2013/0328520 A1 | 12/2013 | Chen et al. |
| 2013/0342028 A1* | 12/2013 | Hermann ............ C02F 1/46104 307/109 |
| 2014/0312828 A1 | 10/2014 | Vo et al. |

FOREIGN PATENT DOCUMENTS

| | | |
|---|---|---|
| JP | 2010045093 A | 2/2010 |
| JP | 2014011303 A | 1/2014 |
| TW | 200610446 A | 3/2006 |
| TW | I435658 B | 4/2014 |

* cited by examiner

HIGH DYNAMIC RANGE MEASUREMENT SYSTEM FOR PROCESS MONITORING

CROSS-REFERENCE TO RELATED APPLICATIONS

This application is a continuation of U.S. patent application Ser. No. 14/696,370, entitled "HIGH DYNAMIC RANGE MEASUREMENT SYSTEM FOR PROCESS MONITORING", by Larry Arlos Bullock, et al., filed on Apr. 24, 2015, which is commonly assigned with the present application and is incorporated herein by reference as if reproduced herein in its entirety.

TECHNICAL FIELD

The present invention relates to optical measurement systems and methods of use. More particularly, the present invention is directed to an optical measurement system configured to decrease sources of variation and extend dynamic range of measurement capabilities in a flashlamp-based optical measurement system.

BACKGROUND

Optical measurement systems are employed in a variety of industries, such as the semiconductor processing industry, for real-time monitoring of wafer modification and process control. Optical measurement systems may be integrated with a semiconductor processing tool and may be utilized in-situ for real-time process control or in-line for run-to-run feedback control. Typically, monitored processes include semiconductor etching, deposition, implantation and chemical mechanical planararization processes for film thickness and plasma monitoring applications.

Especially in the semiconductor processing industry, the use of increasingly variable material layers and features sizes (thinner/thicker layers, high aspect ratio features, very small features, mixed size features, highly variable reflectivity/absorption materials, and high layer count stacks) has led to difficulties in achieving necessary levels of measurement accuracy and precision. In addition to the increasing complexity of the semiconductors themselves, highly integrated single chamber multiple step processes and dynamic processing tool changes of mechanical parameters (e.g., aperture and working distances) cause variation in optical signal levels adversely affecting measurement accuracy and precision.

FIG. 1 shows a pictorial schematic of a typical prior art optical measurement system 100. Optical measurement system 100 includes light analyzing device 110, light source 120, optical assembly 130, optical fiber assembly 140, computer 150 and wafer 160. Light analyzing device 110 is commonly a spectrograph, spectrometer, monochromator or other light analyzing device providing wavelength discrimination. Light source 120 is either a continuous broadband emission source (e.g., tungsten halogen lamp or deuterium lamp) or a pulsed broadband emission source such as a xenon flashlamp. Optionally, narrowband continuous or pulsed emission sources such as lasers and/or light emitting diodes are used. Optical assembly 130 is designed to direct light of one or more wavelengths emitted from light source 120 onto wafer 160 which is typically a silicon semiconductor wafer, sapphire substrate or other workpiece. Optical assembly 130 commonly acts to either focus or collimate light from light source 120 onto wafer 160. Optical fiber assembly 140 is commonly a bifurcated optical fiber assembly which directs light from light source 120 to wafer 160 via optical assembly 130 and subsequently directs light collected upon reflection from wafer 160 via optical assembly 130 to light analyzing device 110. Computer 150 is used to control light analyzing device 110 and light source 120 and is also used to analyze data collected by light analyzing device 110. Computer 150 may also provide signals to control external systems such as semiconductor processing tools (not shown).

Reflectometry in the form of interferometric endpointing is widely used in the semiconductor industry for monitoring the state of a wafer process within a semiconductor processing tool by using optical signals reflected from a wafer being modified within the processing tool. While interferometric endpointing techniques may vary with the particular application and process, typically the light emission intensities are monitored at one or more predetermined wavelengths. Depending on the process, various algorithms may be employed for deriving trend parameters, often related to thicknesses of various layers or features of the wafer, from the light intensities that are useful in assessing the state of the semiconductor process and the in-process wafer, detecting faults associated with the process, processing tool or other equipment. Although commonly named "endpointing" and historically implying the detection of the end of a process; interferometric endpointing has evolved to include monitoring and measurement during all times of a process cycle.

With specific regard to monitoring and evaluating the state of a wafer within a processing tool, FIG. 2 illustrates a typical prior art process 200 for employing interferometric endpointing to monitor and/or control the state of a workpiece within a plasma processing tool. The present method is greatly simplified for expedience. Details of certain processes and implementations are provided by review of US Patent Application Number 20130016343, included herein by reference. Process 200 typically begins by directing light onto the workpiece of interest (step 210). Light directed onto the workpiece is then reflected from that workpiece (step 220) and subsequently detected (step 230). Detection is commonly associated with conversion to electrical signals, the signals are typically amplified and then digitized and passed to a signal processor for analysis (step 240). The signal processor employs one of more algorithms that is/are specific to the particular production process and the characteristics of the workpiece being monitored. The selection of the proper algorithm, as well as parameter values, for the particular process is imperative to achieving a valid result. Without being too specific, the algorithm analyzes intensity signals and determines trend parameters that relate to the state of the process and can be used to access that state, for instance, end point detection, etch depth, film thickness, faults, plasma instability, etc. (step 250). The results are output (step 260) for use by external control systems and/or engineers and then used for monitoring and/or modifying the production process occurring within the plasma processing tool (step 270).

SUMMARY

In one aspect, the disclosure provides a digital flashlamp controller. In one embodiment, the digital flashlamp controller includes: (1) a trigger interface configured to provide firing signals to control a trigger element for a flashlamp bulb and (2) digital electronics configured to generate the firing signals and control multiple pulsing of the flashlamp bulb.

In another aspect, a flashlamp control system is disclosed. In one embodiment, the flashlamp control system includes: (1) a high voltage power supply, (2) digital control electronics for controlling a duty cycle, frequency and pulse width of the high voltage power supply, (3) at least one capacitor electrically connected to the high voltage power supply, (4) a trigger element controlled by the digital control electronics, and (5) a flashlamp bulb electrically connected to the high voltage power supply.

In yet another aspect, a method of controlling a flashlamp bulb employing digital control electronics is disclosed. In one embodiment, the method includes: (1) determining a power supply drive frequency, pulse width and duty cycle for a capacitor based on an active discharge capacitor value and configuration thereof, wherein the capacitor is electrically connected between a high voltage power supply and the flashlamp bulb, (2) generating a plurality of current pulses at the high voltage power supply by the digital control electronics based on the power supply drive frequency, pulse width and duty cycle, and (3) charging the capacitor employing the plurality of current pulses from the high voltage power supply.

BRIEF DESCRIPTION

Reference is now made to the following descriptions taken in conjunction with the accompanying drawings, in which: The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

Figure 7:
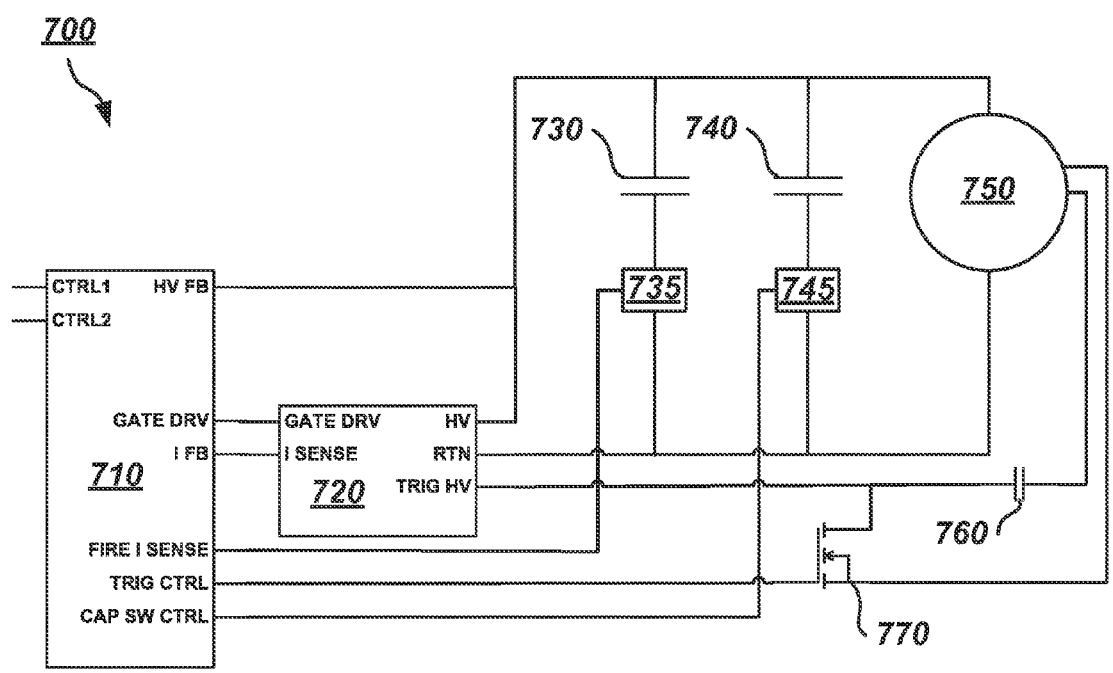
FIG. 7 is a simplified electrical schematic of an improved flashlamp control system configurable for use with an optical measurement system, in accordance with an exemplary embodiment of the present invention.
Figure 9A:
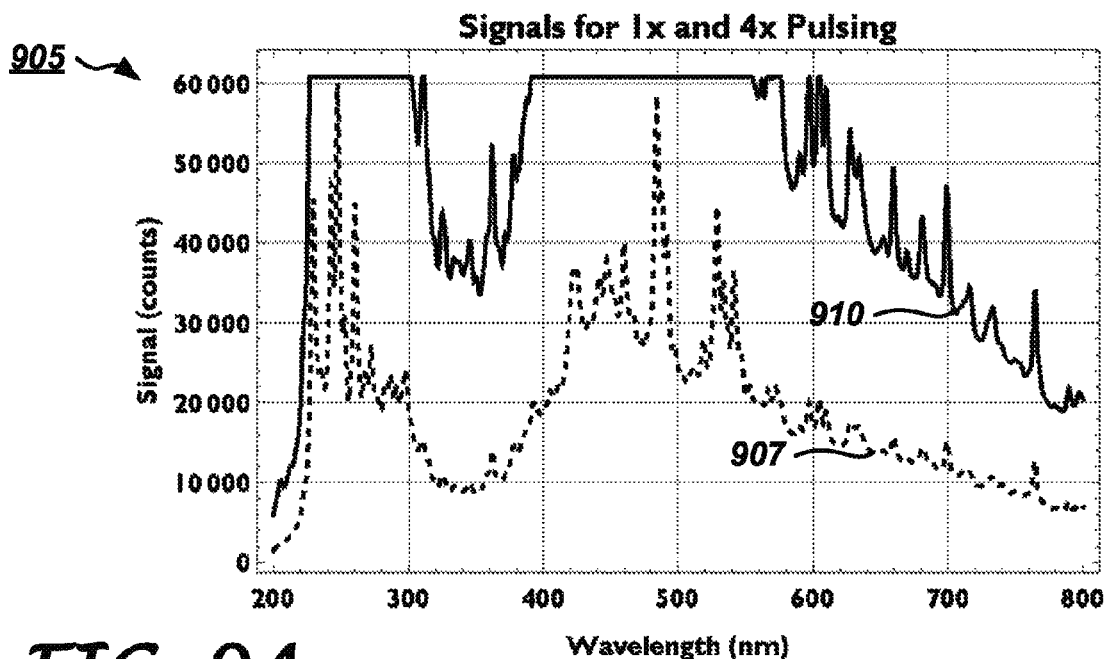
Figure 9B:
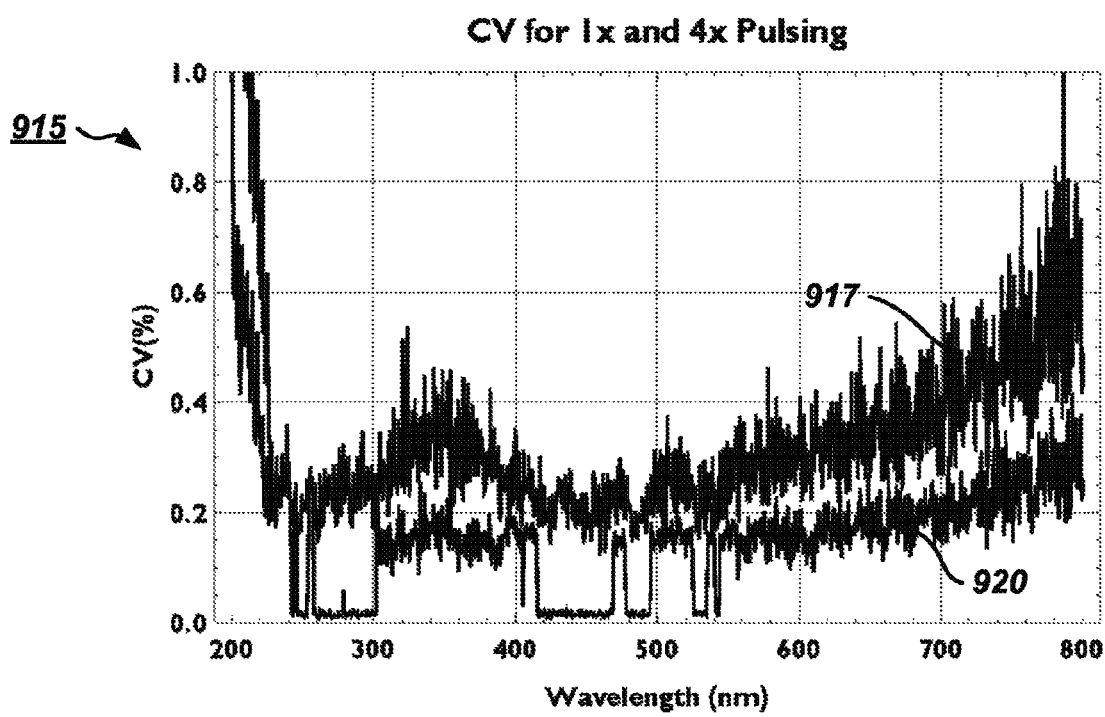
Figure 9C:
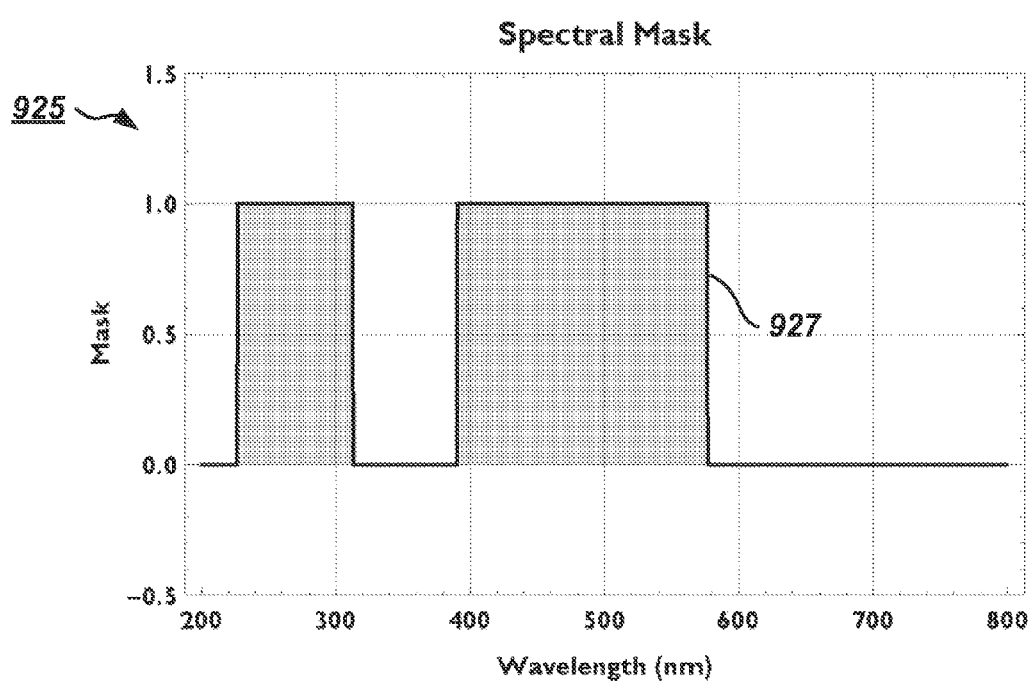
Figure 9D:
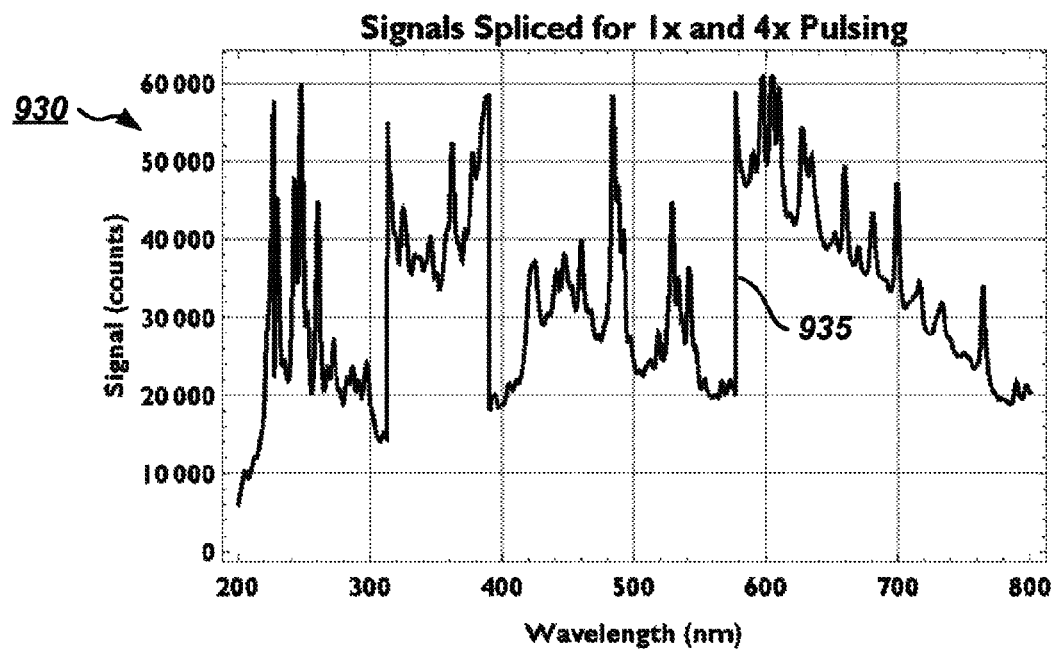
Figure 9E:
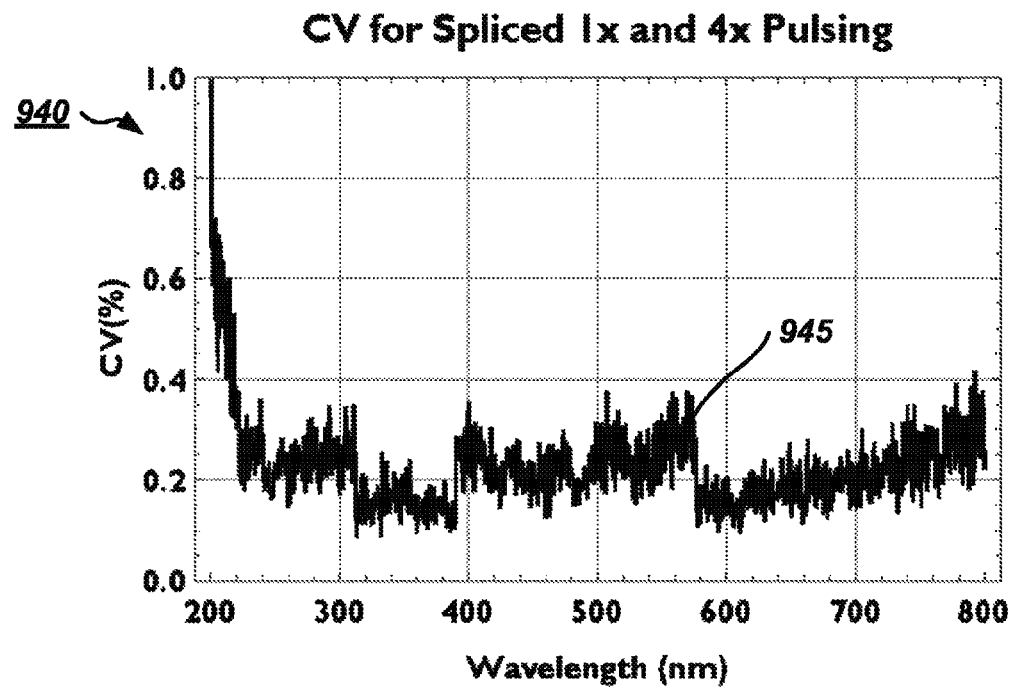
Figure 10:
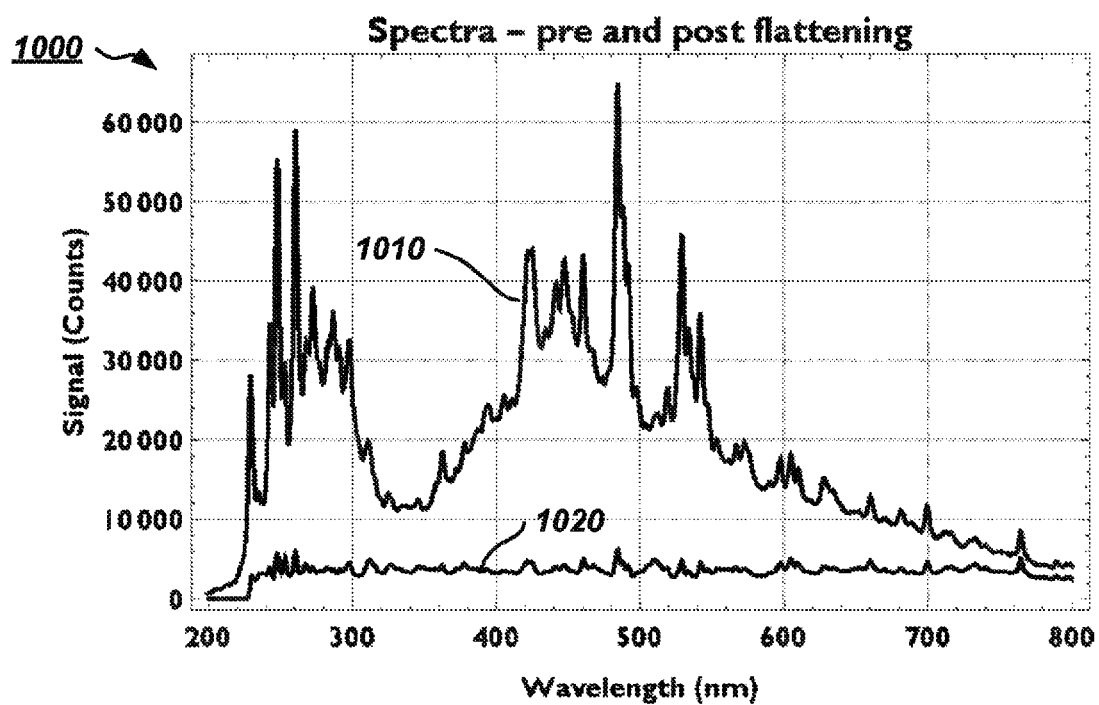

FIGS. 9A-9E show a set of plots detailing the construction of a composite high dynamic range signal provided by the functionality of an optical measurement system incorporating the flashlamp control system of FIG. 7, in accordance with an exemplary embodiment of the present invention; and FIG. 10 shows a plot of the performance of the addition of a spectral flattening filter configurable for use with an optical measurement system, in accordance with an exemplary embodiment of the present invention.

DETAILED DESCRIPTION

In the following description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following description is, therefore, not to be taken in a limiting sense. For clarity of exposition, like features shown in the accompanying drawings are indicated with like reference numerals and similar features as shown in alternate embodiments in the drawings are indicated with similar reference numerals. Other features of the present invention will be apparent from the accompanying drawings and from the following detailed description. It is noted that, for purposes of illustrative clarity, certain elements in the drawings may not be drawn to scale.

Prior art systems, such as optical measurement system 100, are subject to multiple herein-mentioned variations and limitations and have limited suitability for high repeatability and high accuracy optical measurements, which limits their functionality for current state-of-the-art in situ and/or inline applications. To overcome the shortcomings of prior art systems, the present invention generally includes a system and method for optical measurement which compensates for the deleterious effects of limited dynamic range and variable signal attenuation as well as compensating for other system drift and variation. More specifically, the present invention addresses: (1) increasing the dynamic range of optical measurement systems, (2) improving the stability of optical measurement systems for better optical measurement resolution and accuracy, and (3) providing these previous aspects in a multi-channel way. Other advantages of the current invention will be described below in association with embodiments.

Figure 2:
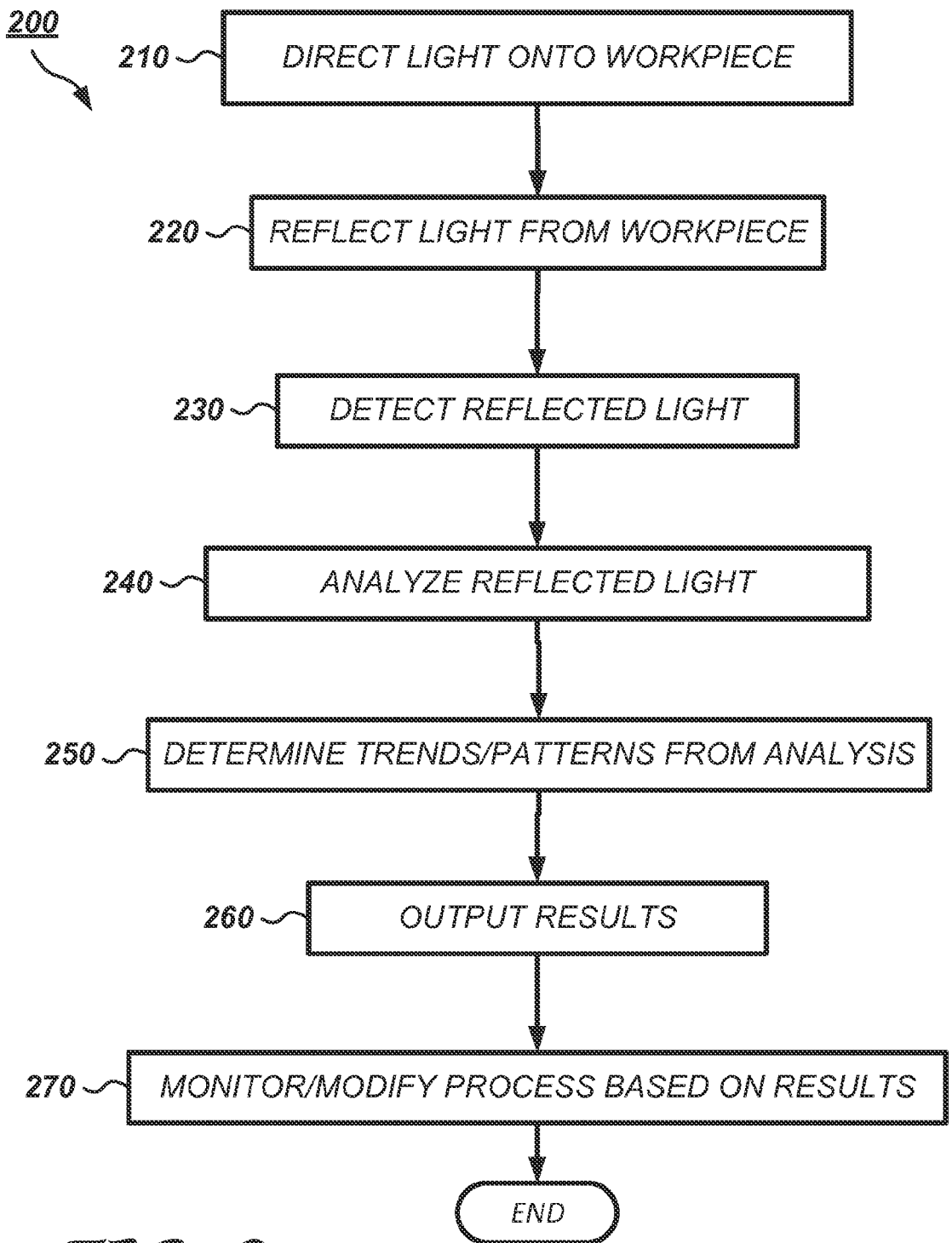
FIG. 2 illustrates a typical prior art process for employing interferometric endpointing to monitor and/or control the state of a wafer within a processing tool.

The adjustability of prior art optical measurement systems is commonly based upon a limited set of operational parameters including manual changes to flashlamp capacitors, programmable flashlamp voltage control and/or configurable spectrometer integration time. These prior art systems and their restrictive operational parameters become insufficient as the complexity of monitored processes increases as driven by the needs of state-of-the-art semiconductor processing equipment and integrated processes. Furthermore, although the generic method discussed above with regard to FIG. 2 is useful in monitoring/evaluating many different processes; the increasing precision, accuracy and variability of processes demand constant increases in dynamic range and noise reduction whereby adding further complexity and requirements to optical measurement systems and processes.

Figure 3A:
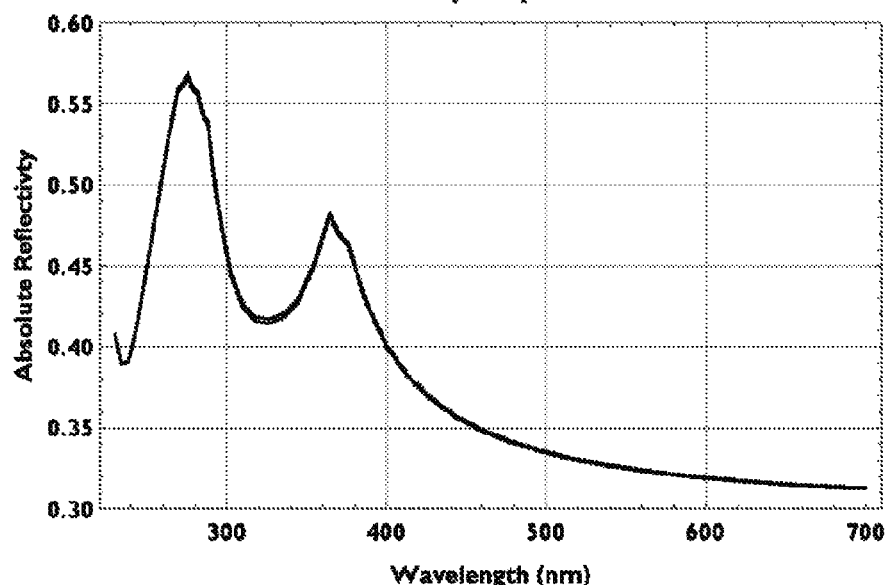
FIGS. 3A and 3B show a set of plots representing challenges inherent in measurement of the reflectivity of thin films and the differences in reflectivity detection desired for high precision semiconductor processes and addressable, in accordance with an exemplary embodiment of the present invention.
Figure 3B:
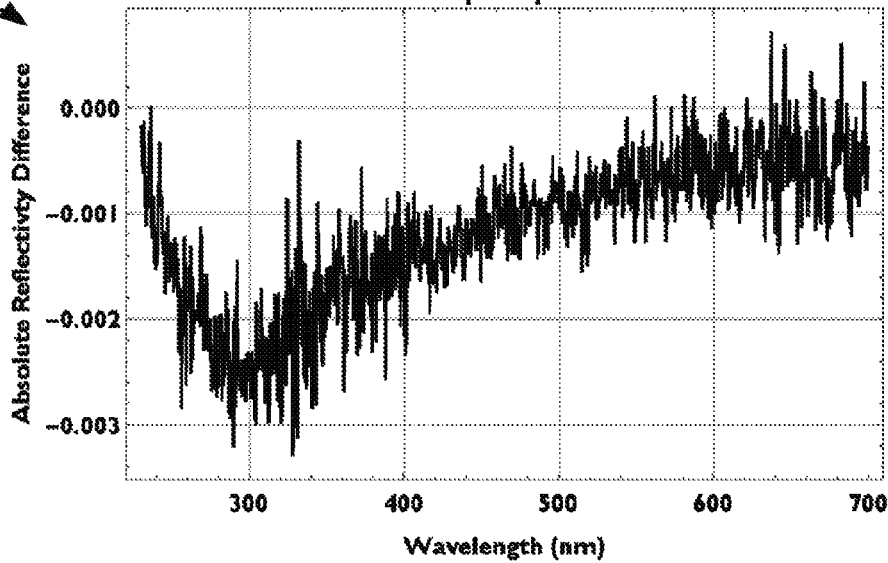

FIGS. 3A and 3B show a set of plots 300 and 350, respectively, representing the reflectivity of thin films and the differences in reflectivity detection required for high precision monitoring of semiconductor processes. The example here of blanket silicon dioxide films deposited upon a crystalline silicon substrate is a simplification of often very complex multilayer patterned film stacks but is nonetheless used as a reference and test geometry especially with commonly used "monitor wafers." Plot 300 shows the theoretical absolute reflectivity versus wavelength for 300 and 305 Angstrom thick blanket silicon dioxide films deposited upon a crystalline silicon substrate. As plotted the reflectances are essentially indistinguishable except near wavelengths of approximately 350 nanometers. Remarkably, this difference in film thickness is comparable to only two monolayers of crystalline silicon, and larger than two monolayers of silicon dioxide. These very thin films and the strict requirements upon their extremely high accuracy and precision of film thickness determination are required for advanced applications such as 3D NAND memory and gate structures in high speed processors. Required control levels for film thickness are often at the level of 1 Angstrom. Although precision and accuracy of thickness measurement at this level has historically required the application of spectroscopic ellipsometry; the novel optical measurement system of the present invention also provides this level of measurement precision and consequent process control.

Plot 350 shows a difference spectrum for the 300 and 305 Angstrom thick films represented in plot 300 experimentally obtained from an optical measurement system of the present invention. For 5 Angstrom precision, the signal to noise must be approximately greater than 200:1 and for 1 Angstrom precision greater than 1000:1. Maximal reflectance differences, near 300 nanometer wavelength are less than 0.5% for 5 Angstrom and less than 0.1% for 1 Angstrom differences in film thickness. Although a single static measurement is indicated here, repeatability across multiple measurements, from multiple points upon the same wafer and across multiple semiconductor processing tools is required and further tightens the dynamic range, signal-to-noise, channel-to-channel variation and other requirements. The limitations inherent in existing prior art flashlamp based optical metrology systems and specifically in the implementation of the flashlamps themselves inhibit obtaining required repeatability, uniformity, precision and accuracy.

Figure 1:
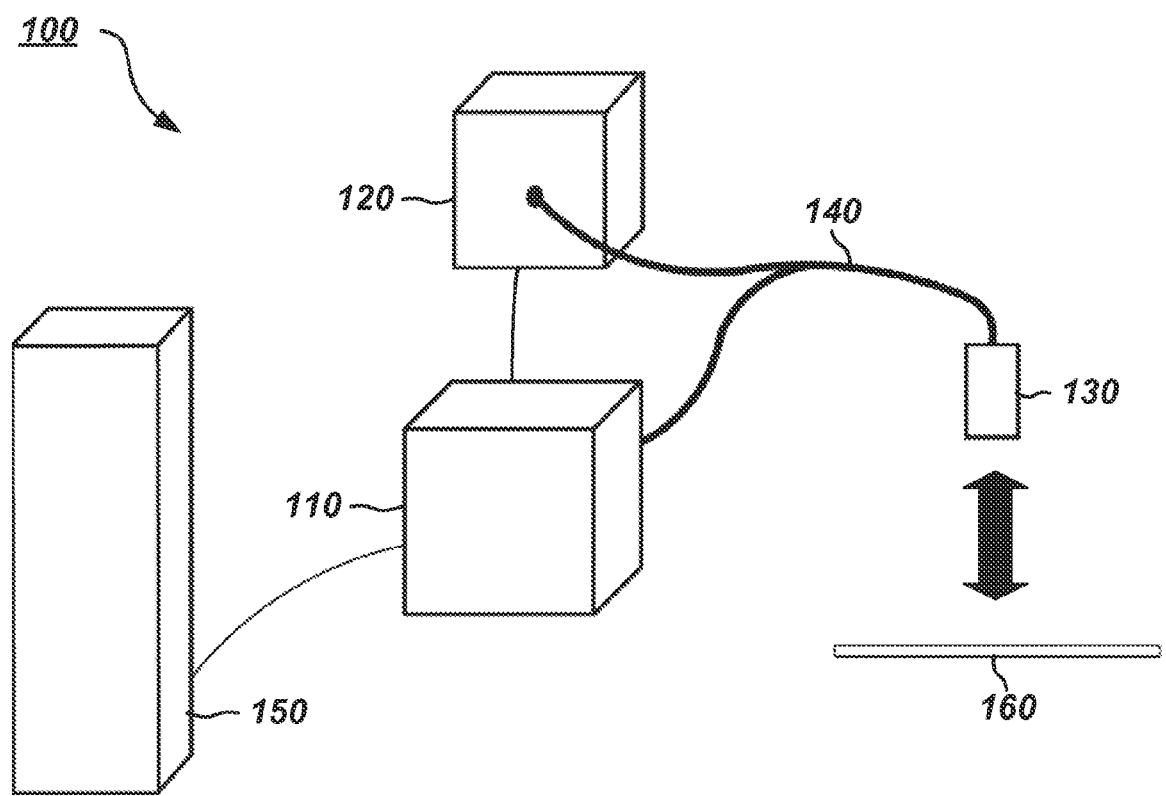
FIG. 1 is a pictorial schematic of a prior art optical measurement system.
Figure 4:
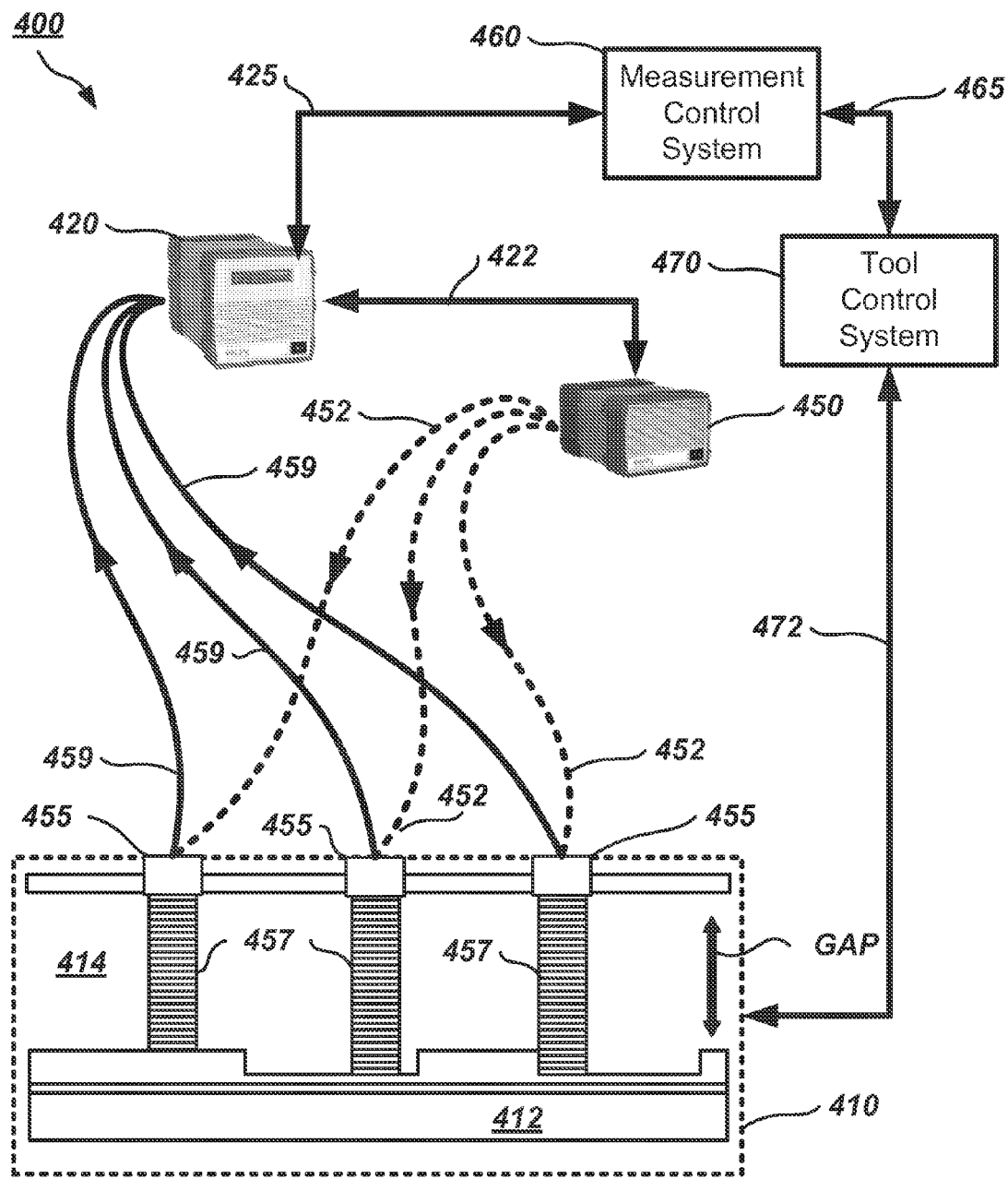
FIG. 4 shows a pictorial schematic of a semiconductor processing tool including an optical measurement system, in accordance with an exemplary embodiment of the present invention.

FIG. 4 shows a pictorial schematic 400 of an integration of a semiconductor processing tool and an optical measurement system of the present invention. The system depicted here may be contrasted to the prior system depicted in FIG. 1 to permit discussion and motivation for interferometric endpointing innovation to accommodate the dynamic tool conditions, multiple point measurement uniformity, multiple-film-single-chamber processes, etc. Critically, it should be noted that prior art optical measurement systems typically implement a single measurement channel. Similarly, associated processing tools commonly accomplish only a single process step. Advances in processing tool flexibility and process methodologies for larger wafers now require additional configurability in optical metrology systems in order to support increased operational parameters. For example, processing tools may change the gap (plasma space) and multiple measurement locations may be affected by mechanical and/or thermal variations driven by processing tool changes. Furthermore, continuous metrology may be required in place of common prior art "endpointing" for process stop.

System 400 includes major components: processing chamber 410, spectrometer 420, flashlamp 450, measurement control system 460 and tool control system 470. Processing chamber 410 encloses wafer 412 in plasma volume 414. Flashlamp 450 provides light to one or more fibers 452 (indicated by dashed lines) which guide the light toward optics 455 which are used to define the optical beams 457 and the measurement spot size upon the surface of wafer 412. As wafer sizes increase from 200 mm to 300 mm and soon to 450 mm, more locations for measurement are needed to characterize the non-uniformity of the monitored process. This requires simultaneous control over the various optical signal levels in order to assure uniformity across the measurement locations. All optical signal levels must be precisely controlled for proper signal-to-noise, enabling the desired accuracy and precision of the resultant characterization, for example, film thickness determination.

Upon reflection from wafer 412 optical signals are transmitted via signal optical fibers 459 (indicated by solid lines) to spectrometer 420 for wavelength discrimination and conversion to electrical and/or digital signals. Spectrometer 420 may, for example, include a grating for wavelength discrimination and CCD or CMOS optical sensors for collection of optical signals. Fibers 459 may vary in length and make-up to allow for accessing the various locations of wafer 412 and may include attenuators to adjust each signal and accommodate overall signal level differences due to length, processing tool impacts or other factors. Spectrometer 420 may send and receive commands and other information to and from flashlamp 450 via interconnect 422. These commands may include lamp power level, flash rates, errors, multiple pulsing configurations, etc. as discussed herein. Spectrometer 420 may also communicate with measurement control system 460, commonly an industrial PC via communication link 425 which may be use Ethernet, USB, EtherCAT or other systems and protocols. Alternatively measurement control system 460 may be embedded into spectrometer 420 as a unified assembly. Spectrometer and/or measurement control system 460 may communicate via link 465 with tool control system 470 which itself communicates/controls via link 472 with processing chamber 410 and other elements (not shown) of the processing tool and semiconductor manufacturing facility.

Figure 5A:
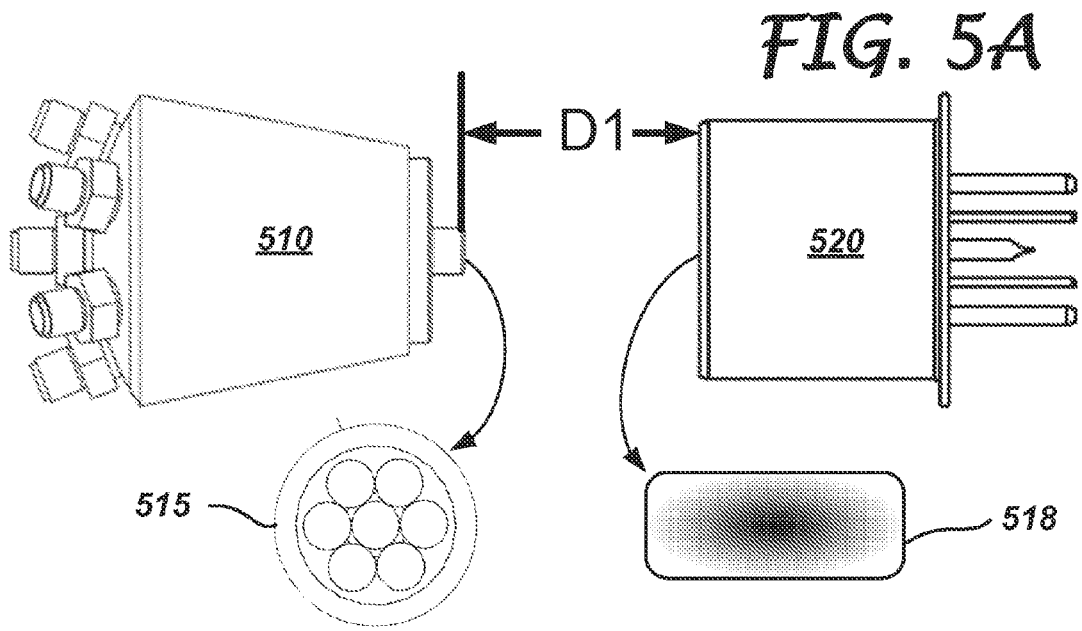
FIGS. 5A, 5B and 5C are a set of three cross-sectional views of exemplary construction of an improved optical assembly interfacing with a flashlamp configurable for use with an optical measurement system, in accordance with an exemplary embodiment of the present invention.
Figure 5B:
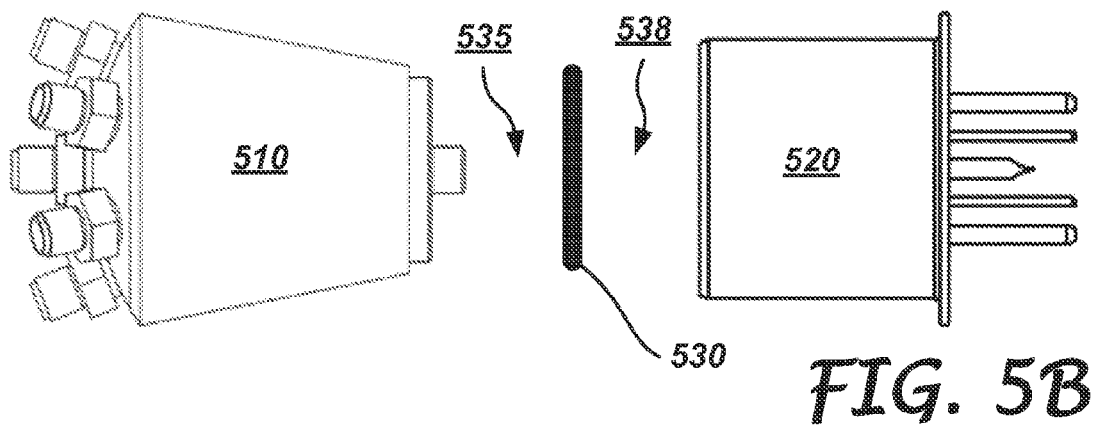
Figure 5C:
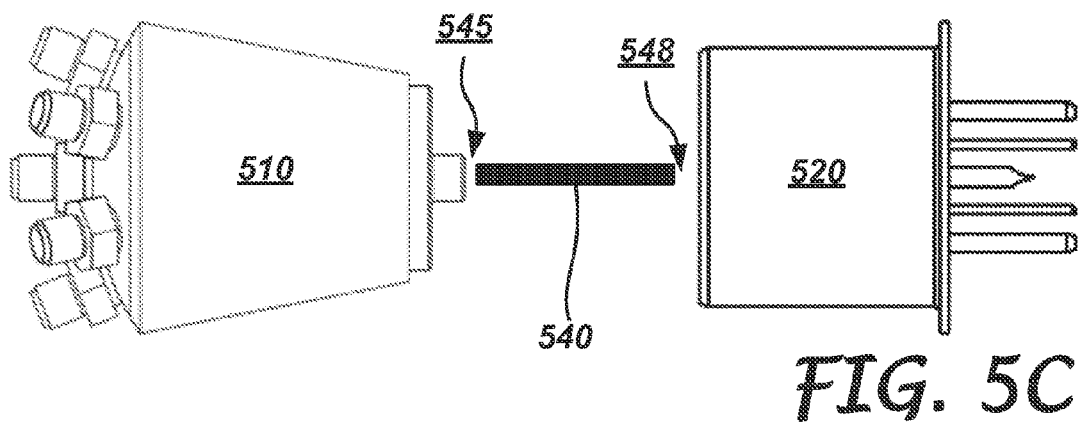

Flashlamps are advantageous components of optical measurement systems due to their pulsed operation, brightness, controllability and cost. However, flashlamps can be significant sources of temporal and spectral variation. An aspect of the present invention is to address those variations inherent in flashlamps to extend their usability by increasing homogenization, reducing shot-to-shot temporal and spectral variability and improving channel-to-channel uniformity for multipoint measurement systems. FIGS. 5A, 5B and 5C are a set of three cross-sectional views of exemplary construction of an improved optical assembly interfacing with a flashlamp configurable for use with an optical measurement system and flashlamp 450, such as described in association with FIG. 4. In multipoint measurement systems, again with reference to FIG. 4, the optical output of flashlamp may be mapped onto a suitable multichannel distributor. In FIGS. 5A, 5B and 5C multichannel distributor 510 provides 1×N distribution of the optical signal provided by flashlamp bulb 520 and integrates the fiber connections to optical fibers such as fibers 452 of FIG. 4. Although FIGS. 5A, 5B and 5C show specific flashlamp bulb 520, and multichannel distributor 510 including 7 fiber with SMA connection; it should be understood that greater or fewer fibers are possible and that different flashlamp bulbs and fiber connections may be utilized.

Historically, for highest signal coupling common end of distributor 510 is positioned as close as possible to face of flashlamp bulb 520. Although this may provide the highest overall signal coupling efficiency; the relative size of fiber bundle 515 and lamp arc 518 may contribute to high channel-to-channel non-uniformity (see FIG. 6A system configurations #1 and #2) due to angular and geometric size mismatch. For example, a 400 micron core fiber designed into a hexagonal closed packed array as shown in bundle 515 has a diameter of approximately 1.35 mm; whereas the spatial extent of the lamp arc 518 is an approximately 1×2 mm flat-topped rectangular Gaussian profile. Furthermore the angular emission profile of the flashlamp bulb and the numerical aperture of the individual fibers of bundle 515 are often incongruous. Partial optimization may be achieved by selectively altering distance D1 between distributor 510 and lamp 520. This partial optimization comes at the expense of signal level. Signal level may be adjusted by increasing lamp output but this promotes a shorter lifetime of the lamp and is ultimately undesirable. Experimentation indicates that distance D1 may be set within the range of approximately 0.0 to 0.5 inches and more preferably to a range of 0.2 to 0.3 inches to achieve improved homogenization and channel-to-channel non-uniformity.

FIG. 5B shows the inclusion of a first type of homogenizing element 530. Specifically element 530 may be, for example, a single- or double-sided ground glass diffuser, fly-eye lens assembly, holographic diffuser, microlens array or other imaging or non-imaging homogenizer including volume homogenizers. Homogenizing element 530 also provides partial homogenization at the cost of signal level since considerable light may be scattered and significant distances may be required to permit element 530 to function properly. Experimentation indicates that for ground glass diffusers, such as from Thorlabs of Newton, N.J. gaps 535 and 538 may be set within the range of approximately 0.0 to 0.5 inches and more preferably to a range of 0.2 to 0.3 inches for gap 535 and 0.0 for gap 538 respectively to achieve improved homogenization and channel-to-channel non-uniformity. The application of homogenizing element and appropriate gaps may be readily applicable in cases where excessive light is available since it is advantageous to operate the lamp at mid-range power levels for best performance and therefore efficiency may not be critical.

FIG. 5C shows a second class of homogenizing element, light pipe 540, integrated between distributor 510 and bulb 520. Light pipe 540 functions differently than homogenizing element 530 or inclusion of gap D1 and provides homogenization with limited loss of signal level. For proper functioning of light pipe 540, gaps 545 and 548 must be carefully controlled and coaxial alignment of bulb 520, light pipe 540 and distributor 510 must be maintained for proper filling of light pipe 540 and interception of the homogenized signal onto distributor 510. In a specific embodiment, gaps 545 and 548 may be set within the range of approximately 0.0 to 0.5 inches and more preferably to a range of 0.05 to 0.25 inches for gap 545 and 0.0 for gap 548 respectively to achieve improved homogenization and channel-to-channel non-uniformity for a 2 mm fused silica light pipe such as from Edmund Optics of Barrington, N.J. It should be noted that each method of homogenization discussed herein above in association with FIGS. 5A-5C provide improved homogenization but selective use conditions must be considered to balance the light loss. Although transmissive optical elements are discussed hereinabove; it should be understood that reflective equivalents may exist and may be substituted.

Figure 6A:
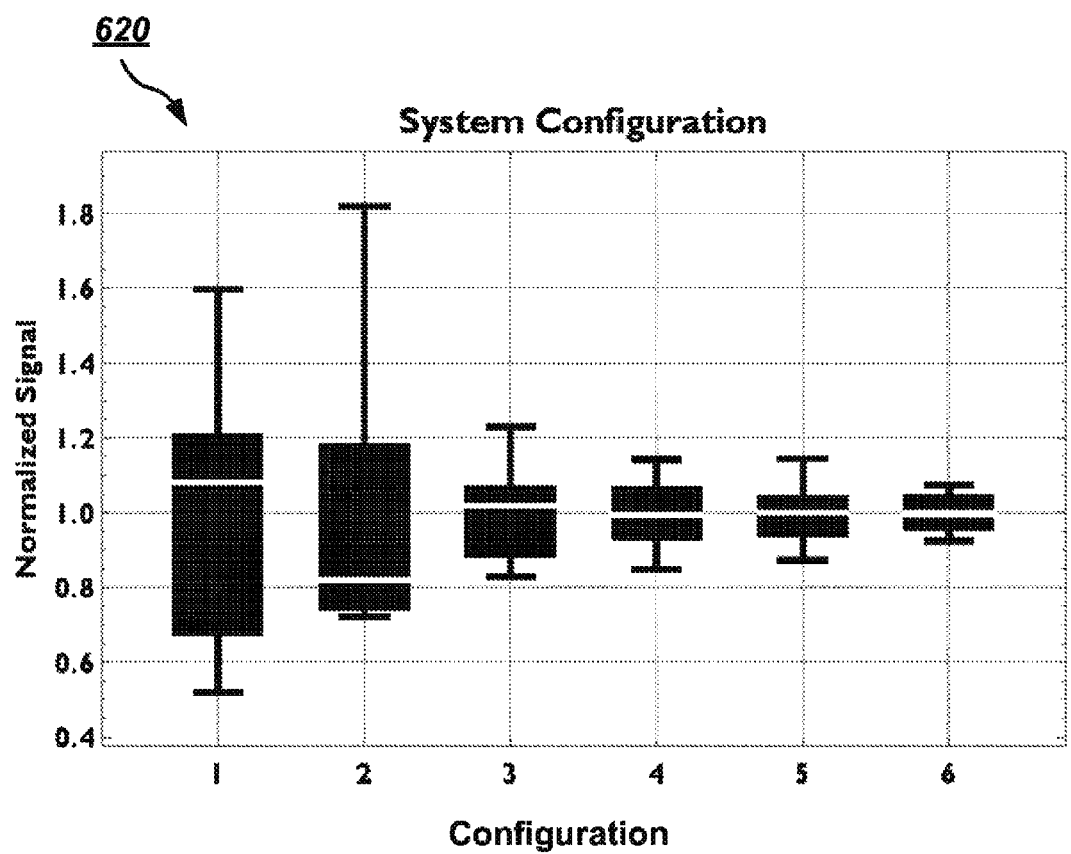
FIGS. 6A, 6B and 6C show a set of plots comparing the performance of a prior art optical measurement system and a flashlamp and optical assembly, in accordance with an exemplary embodiment of the present invention.
Figure 6B:
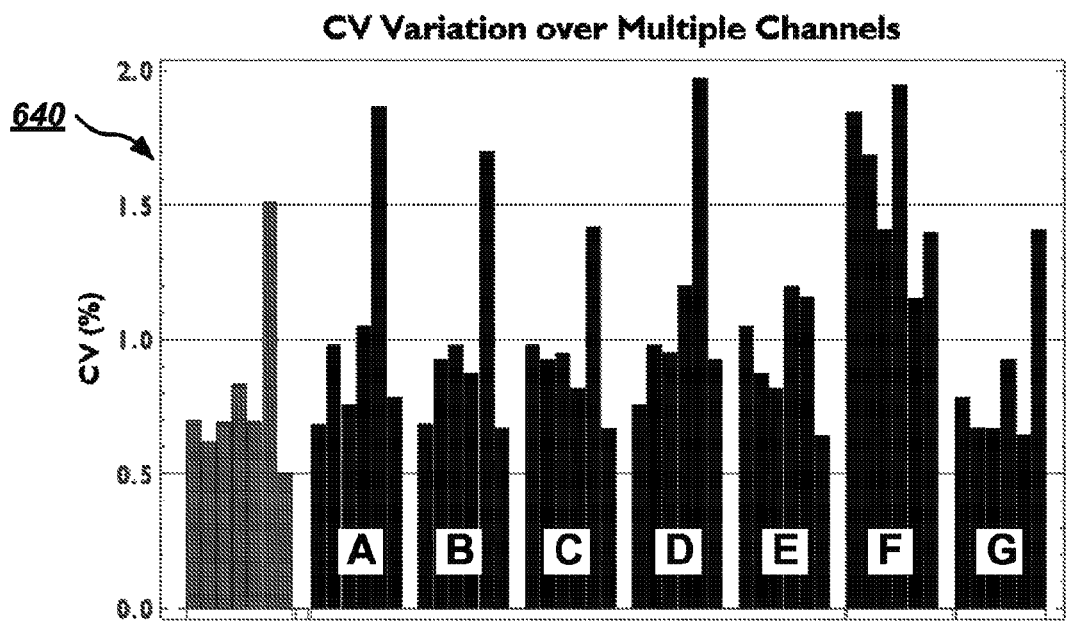
Figure 6C:
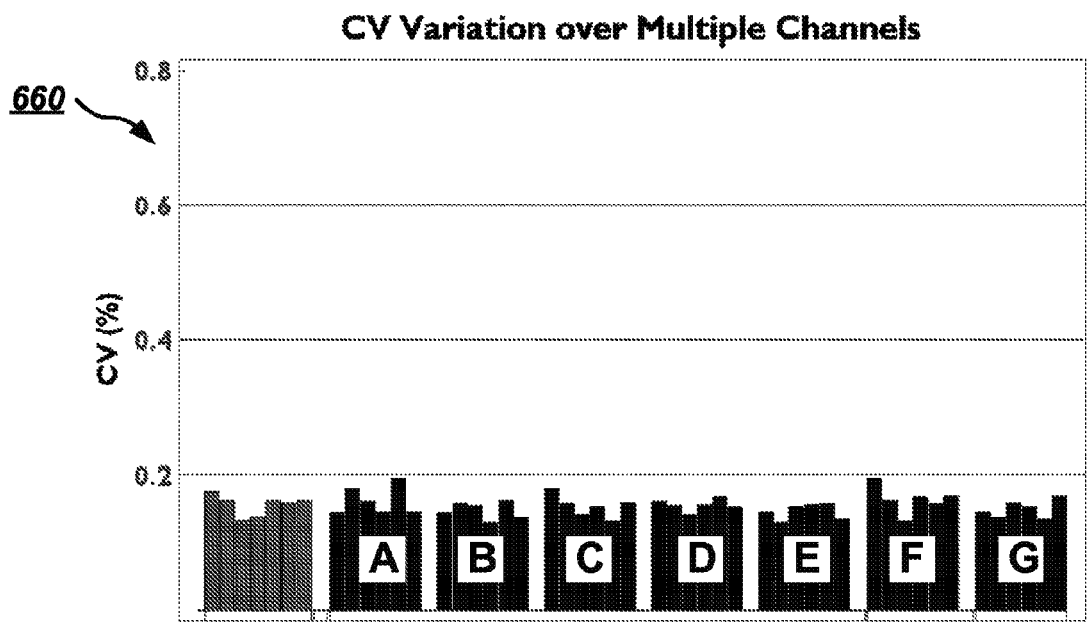

FIGS. 6A, 6B and 6C show a set of plots comparing the performance of a prior art system and a flashlamp and optical assembly in accordance with an exemplary embodiment of the present invention. Optical signal homogenization directly affects both channel-to-channel uniformity and the variation within each individual channel. Although the wavelength-dependent optical signal enters into the reflectance and ultimate thickness measurement via complex trigonometric functions, the variation in the reflectance and/or thickness measurement may be estimated as proportional to the variation in the optical signals. These plots show the improvements possible with the application of varied types of homogenization elements incorporated between the flashlamp bulb and multichannel distributor as shown in FIGS. 5A-5C. Specifically, FIG. 6A shows a plot 620 of the channel-to-channel uniformity and FIGS. 6B and 6C are within-channel improvements in coefficient of variation ("CV") with and without referencing. The box and whisker chart of FIG. 6A compares channel-to-channel uniformity amongst the prior art unhomogenized interfaces (configurations #1 and #2), diffusing homogenizing elements (configurations #3 and 4) and homogenizing light pipe elements (configurations #5 and #6). Values for plot 620 are derived from wavelength-averaged signals from a set of seven individual channels. Configuration #3 represents a diffusing homogenizing element with smaller gaps for higher signal levels and results in poorer homogenization and therefor lower channel-to-channel uniformity. Configuration #4 represents a diffusing homogenizing element with gaps optimized for best uniformity. Configuration #5 represents a light pipe homogenizing element with a gap near the distributor slightly too large and configuration #6 represents a light pipe homogenizing element with optimized gaps. Experiments indicate that a light pipe homogenizing element should be positioned so that it is essentially butted to the surface of the flashlamp bulb and approximately one diameter (~2 mm) from the distributor. It should be understood that light pipe diameter and position will depend upon factors such as bulb arc size, number and diameter of the fibers in the distributor, etc.

FIG. 6B shows a plot of the within-channel and cross-channel performance of a prior art seven channel system optical measurement system. For this system six channels are used for actual measurement and a seventh channel is used for referencing the other channels for the mitigation of signal drift and other effects. In plot 640, the seven channels of data are analyzed for variation individually (indicated by the leftmost 7 bars) and then pairwise via wavelength by wavelength division for referencing (indicated by individual bars of columns A-G). CV (coefficient of variation) values presented are averaged over the wavelength range of ~300-700 nm. Individually the variation for each channel is ~0.75% and the sixth channel is much worse at ~1.5%. Considering the proportionality of the variation of the optical signal to the variation of resolved film thickness; it may be seen that the 0.75% is insufficient to support the determination of the required 1 Angstrom resolution discussed hereinabove which requires ~0.1% variation. For convenience of operation, it is expected that all outputs from a distributor be equivalent but in the case of the prior art this is not observed. Furthermore, when cross-channel variation is determined (columns A-G of plot 640), it is observed that correlation between channels is sufficiently low that for all combinations the variation is actually increased so that although referencing may aid in the mitigation of optical signal drift; the optical signal variation and therefore the thickness resolution is negatively impacted.

In contrast to the data of FIG. 6B, the data of FIG. 6C shown in plot 660 of the performance of a system of the present invention including an optimized light pipe homogenizing element shows marked improvement. All within-channel variation is greatly reduced and paired cross-channel variation is similarly reduced and in some cases the correlation is now sufficiently high to permit the referencing to further reduce the variation as well as controlling drift.

FIG. 7 is a simplified electrical schematic of flashlamp control system 700 configurable for use with an optical measurement system, in accordance with an exemplary embodiment of the present invention. FIG. 7 represents the primary elements required for operation of flashlamp control system 700. Commonly known and used secondary elements such as signal conditioning components, filter capacitors, DC-DC convertors, etc. are not displayed for clarity of the primary elements. The schematic indicates the essential components of an improved dynamically adjustable, by internal and external digital electronic means, flashlamp control system. This is in contrast to fixed, static prior art systems such as shown in U.S. Pat. No. 3,780,344, included herein by reference.

Control system 700 includes configurable digital control electronics 710 which provide interfacing to both internal and external components such as spectrometer 420 of FIG. 4 and internal high voltage power supply 720. Flashlamp control system 700 may also include any number of static capacitors 730 (only one is shown for simplicity) and any number of dynamically electronically switchable capacitors 740 (only one is shown for simplicity). It should be understood that parallel and serial combinations of capacitors 730 and 740 are possible. Static capacitor 730 may be serially connected with a current sensing component 735 which may be used to detect correct or faulty operation for charging and discharge of the capacitor and providing feedback via digital control electronics 710 to internal and external systems for example to indicate a proper or improper lamp discharge. In accordance with other exemplary embodiments of the present invention (not shown in FIG. 7), additional current sensing components may be serially connected with any additional static or dynamically electronically switchable capacitor.

Any dynamically electronically switchable capacitor 740 may be isolated from control system 700 by switching isolation switch 745 during the uncharged state of dynamic capacitor 740. Switch 745 may be, for example, as described herein below. Flashlamp bulb 750 is connected in a parallel arrangement with capacitors 730 and 740. Firing of flashlamp bulb 750 is initiated by a signal from digital control electronics 710 activating triggering transistor 770 whereby discharging trigger capacitor 760 and causing flashlamp bulb 750 to fire.

Prior art references show a variety of different switch configurations for triggering a flashbulb, however, the control circuit to the switch is always analog. The incorporation of flashlamp digital control electronics, in accordance with exemplary embodiments of the present invention, improves flashlamp performance and functionality in five critical areas. It (1) decreases capacitor recharge time (system cycle time), (2) improves flash to flash intensity and spectral stability, (3) extends the usable dynamic range of the system, (4) permits dynamic change of capacitors and lamp output, and (5) provides monitoring for lamp discharge fault conditions. By knowing the active discharge capacitor value and configuration, digital control electronics 710 calculates an optimum power supply drive frequency and duty cycle to charge capacitors 730 and 740 as rapidly as possible within the system power constraints. In the prior art, the typical side effect of rapid charge time is high voltage ripple that results in poor flash intensity and spectral stability. The configurability of digital control electronics 710 prevents this side effect and minimizes high voltage ripple by dynamically changing the drive frequency and duty cycle as the charge voltage of capacitors 730 and 740 nears the designated discharge voltage. The residual high voltage ripple effects from this advanced control scheme are significantly lower than the intrinsic bulb instability, removing high voltage power supply ripple as a cause of flashlamp instability. Although the system dynamic range is limited by the stable voltage operating range of the lamp (typically ~300V-1 kV for this type of lamp), digital control electronics 710 is able to dynamically switch capacitors to greatly expand the stable operating dynamic range of the system while maintaining the lamp within its voltage specification. Since digital control electronics 710 actively monitors system voltages and currents during operation, it can provide fault notifications if abnormal operation of the bulb or system occurs.

Additional features of control system 700 include configuring the primary side switch of high voltage power supply 720 as high power, high voltage metal-oxide-semiconductor field-effect transistor ("MOSFET") device for improved performance and control. Furthermore, the lamp triggering transistor 770 is configured as a high current, high voltage MOSFET device. This specific embodiment provides improved trigger pulse control over traditional silicon-controlled rectifier ("SCR") based circuits. The dynamic capacitor switching is accomplished by switch 745 based upon a configuration of high voltage diodes and SCRs. The unique topology of switch 745 eliminates the distortion in the discharge current waveform due to SCR turn-on times. The capacitors are nominally low-side switched when discharged, so only the charging cycle currents are switched, not affecting the discharge current waveform.

Digital control electronics 710 may be implemented by using a field-programmable-gate-array ("FPGA") such as from Altera or Xilinx, a microcontroller such as a "PIC" series devices from Microchip or an embedded microprocessor such as ARM series devices from Atmel. In one possible embodiment digital control electronics 710 is implemented in a flash-based Xilinx FPGA. This specific implementation provides additional benefits by eliminating boot and initialization issues/delay arising from a SRAM-based device. The configurability and feedback/control capabilities provided by digital control electronics 710 strongly improves upon the historical application of analog control systems.

Figure 8A:
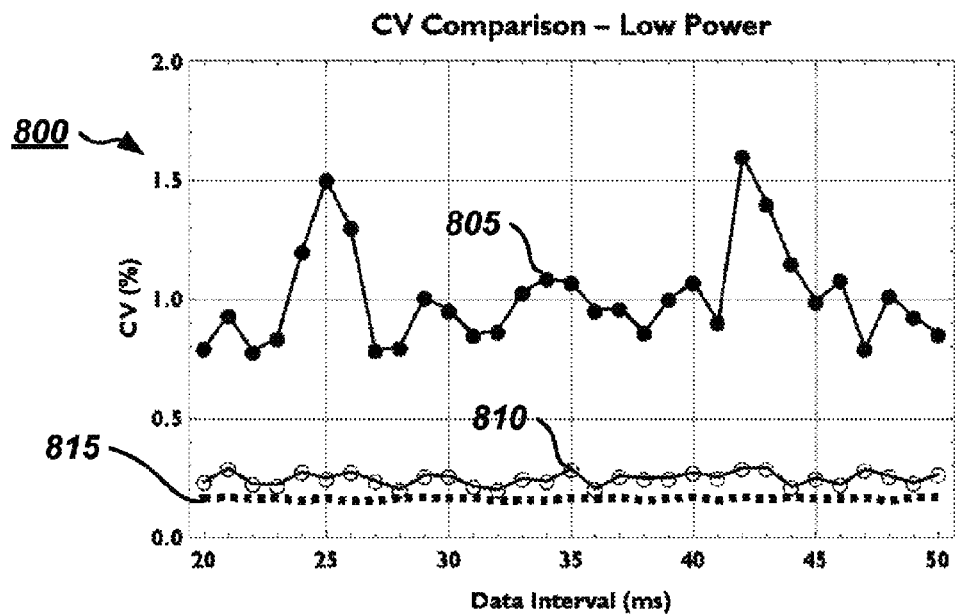
FIGS. 8A and 8B show a set of plots comparing the performance of a prior art optical measurement system and an optical measurement system incorporating a flashlamp modified in accordance with an exemplary embodiment of the present invention.

FIG. 8A shows a plot 800 comparing the performance of a prior art system and a flashlamp modified in accordance with an exemplary embodiment of the present invention. Plot 800 presents a comparison of the wavelength-averaged CV (coefficient of variation as percent of signal averaged over 200-800 nm spectral range) for operation of a flashlamp over three different modes of operation versus data interval. The data are presented for operation at low power (capacitor charge voltages ~350-400V) where the deleterious effects of flashlamp operation are most prevalent. Curve 805 is a reference set of data indicating the performance of prior art system with fixed charging rates and static high voltage power supply conditions. Poor performance of the charging circuit is clearly indicated as it results in overall high CV and considerable structure in curve 805 as the data interval is increased thereby changing is interacting with the recharge rate. The strong structure in curve 805 is due to variations in the charge state of the capacitor varying between each firing in some cases being charged more than expected and in other being charged less than expected. This is specifically notable for ~25 and 45 millisecond recharge periods. Curve 810 shows the markedly improved performance achieved with implementation of the flashlamp control system of FIG. 7. Overall there is a 4×-6× improvement in the CV to approximately 0.25%. This supports the extremely low noise requirements for the high precision and accuracy measurements discussed previously herein in association with FIG. 3. Additionally, curve 815 indicates the additional performance benefits provided by multiple pulsing, in this case 2×, of the flashlamp (enabled by the improvements in control system 700 including digital control electronics 710).

Figure 8B:
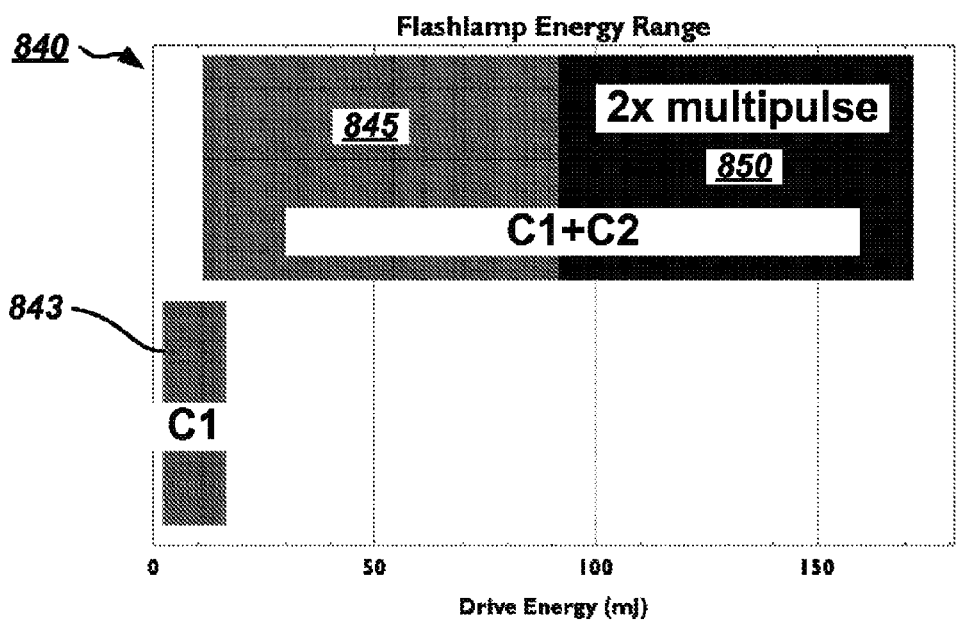

FIG. 8B shows chart 840 of the extended dynamic range provided by the capacitor switching and multiple pulsing improvements of flashlamp control system 700. In chart 840 the log base 10 of the drive energy is plotted versus the configuration of the capacitors. The drive energy is used here as it is proportional to the optical output by a determinable efficiency factor. In the example shown, static small capacitor C1 of 0.033 µF is included with dynamically switchable large capacitor C2 of 0.15 µF. Bar 843 indicates the range of drive energy for capacitor C1 over the drive voltage range 350 to 1000 V corresponding to drive energies of 2 mJ and 16.5 mJ, respectively. Bar 845 indicates both capacitors C1 and C2 switched-on so as to drive the lamp again from with drive charge voltage from 350 to 1000 corresponding to drive energies of 11 mJ and 91.5 mJ, respectively. Bar 850 indicates both capacitors C1 and C2 switched-on so as to drive the lamp with 2× multiple pulsing up to 183 mJ of drive energy. Typical flashlamp operation is limited to a voltage range of 350 to 1000 volts due to operational characteristics for proper excitation of the flashlamp bulb and the drive energy as well as the optical output scales as $E=0.5*C*V*V$. These constraints limit the range of output of traditional systems to from 12.25% to 100% (~8× range) regardless of capacitor size. As may be readily seen, the improvements for dynamic switching and multiple pulsing capabilities provided by the advanced flashlamp control system easily permits output ranges in excess of 90× (183 mJ/2 mJ) with the inclusion of a single switchable capacitor without adverse impact. It should be noted that for prior art fixed flashlamp charging circuits using capacitors of the large ratio as in the described example would result in a compromised solution with poor performance of the small capacitor and/or slow charging times of the large capacitor.

FIGS. 9A-9E show a set of plots detailing the construction of a composite high dynamic range signal provided by the multiple pulsing functionality of the flashlamp control subsystem of FIG. 7 synchronized with optical signal measurement via spectrometer, in accordance with an exemplary embodiment of the present invention. Multiple pulsing permits effective changes in the output signal level of the flashlamp system while maintaining steady state performance and temperature of a fixed energy per flash periodic discharge. Since, as discussed above, shot-to-shot variation is very small and since variable drive voltages are not used each output is nearly identical; combining differently multiply pulsed signals in cooperation with a spectrometer and measurement control system results in a composite high dynamic range signal with decreased CV. FIG. 9A shows plot 905 of exemplary signals 907 and 910 from flash multipliers of 1× and 4× pulsing, respectively. FIG. 9B shows plot 915 of the CVs 917 and 920 of exemplary signals 907 and 910 from the 1× and 4× pulsing, respectively. Although the signal and CV from the 4× multiply pulsed signal is improved over the CV from the 1× pulsing case; certain portions of the original signal are saturated and corresponding portions of the CV are undefined and therefore as a whole the spectrum is not useful for measurement. However, corresponding portions of signal 907 and CV 917 are made available by the synchronization between spectrometer and flashlamp and internal flashlamp control.

FIG. 9C shows plot 925 of a spectral mask used to combine spectra 907 and 910 into a new lower CV and higher dynamic range signal shown in FIG. 9D. Solid curve 927 is the wavelength dependent mask value and shaded portions of plot 925 indicate spectral regions where the multiply pulsed signal 910 is saturated. To use the mask, spectrum 907 is multiplied by the mask and spectrum 910 is multiplied by the additive complement value (1−mask) of the mask. FIG. 9D shows plot 930 of the resultant higher dynamic range spectrum 935 and FIG. 9E shows plot 940 of the resultant CV 945 for the spliced spectra. Comparing FIG. 9E to FIG. 9B an improvement of approximately 2× as indicated by decreased CV may be observed.

FIG. 10 shows plot 1000 of the performance of the addition of a spectral flattening filter configurable for use with an optical measurement system, in accordance with an exemplary embodiment of the present invention. As seen by comparison of unflattened signal 1010 and flattened signal 1020, spectral flattening typically severely decreases signal levels. The complex spectral structure of the output of a xenon flashlamp is particularly difficult to flatten and results in a decrease of approximately 10× in signal level at certain wavelengths. Although, this very significant amount of signal is lost by transmission through the filter, the flattened signal provides and equivalent increase in the dynamic range of an optical measurement system at many wavelengths by more uniform matching the spectral signal to the detection capabilities of the optical measurement device such as a spectrometer. The multiple pulsing capabilities provided by the flashlamp control system of FIG. 7 may be advantageously employed to recover useful signal levels without requiring excessive drive powers for flashlamps.

The changes described above, and others, may be made in the optical measurement systems and subsystems described herein without departing from the scope hereof. For example, although certain examples are described in association with semiconductor wafer processing equipment, it may be understood that the optical measurement systems described herein may be adapted to other types of processing equipment such as roll-to-roll thin film processing, solar cell fabrication or any application where high precision optical measurement may be required. Furthermore, although certain embodiments discussed herein describe the use of a common light analyzing device, such as an imaging spectrograph; it should be understood that multiple light analyzing devices with known relative sensitivity may be utilized. Furthermore, although the term "wafer" has been used herein when describing aspects of the current invention; it should be understood that other types of workpieces such as quartz plates, phase shift masks, LED substrates and other non-semiconductor processing related substrates and workpieces including solid, gaseous and liquid workpieces may be used.

The exemplary embodiments described herein were selected and described in order to best explain the principles of the invention and the practical application, and to enable others of ordinary skill in the art to understand the invention for various embodiments with various modifications as are suited to the particular use contemplated. The particular embodiments described herein are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one of skill in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects all generally referred to herein as a "circuit" or "module." Furthermore, the present invention may take the form of a computer program product on a computer-usable storage medium having computer-usable program code embodied in the medium.

Those skilled in the art to which this application relates will appreciate that other and further additions, deletions, substitutions and modifications may be made to the described embodiments.

What is claimed is:

1. A flashlamp control system comprising:
a high voltage power supply;
at least one capacitor electrically charged by said high voltage power supply, said at least one capacitor having a charge voltage and a designated discharge voltage;
digital control electronics for dynamically changing a drive frequency and duty cycle of said high voltage power supply as said charge voltage of said at least one capacitor approaches said designated discharge voltage within less than a kilovolt difference between said charge voltage and said designated discharge voltage;
a trigger element controlled by said digital control electronics; and
a flashlamp bulb electrically connected to said high voltage power supply.

2. The flashlamp control system as recited in claim 1 wherein said digital control electronics includes a sensing interface configured to receive a feedback control signal that corresponds to a charging or discharging current of said at least one capacitor.

3. The flashlamp control system as recited in claim 2 wherein said digital control electronics is configured to determine a drive frequency, a pulse width and a duty cycle for said high voltage power supply based on said feedback control signal.

4. The flashlamp control system as recited in claim 1 wherein said digital control electronics is further configured to determine a discharge fault of said flashlamp bulb.

5. The flashlamp control system as recited in claim 1 wherein said digital electronics is further configured to actively monitor operation of said flashlamp bulb.

6. The flashlamp control system of claim 1, wherein said digital control electronics controls a recharge rate, an energy level setting and multiple pulsing of said flashlamp bulb.

7. The flashlamp control system of claim 1, wherein said at least one capacitor is a dynamically switchable capacitor and said flashlamp control system further includes an isolation switch electrically connected to said dynamically switchable capacitor and said digital control electronics, wherein said digital control electronics controls operation of said isolation switch.

8. The flashlamp control system as recited in claim 7 wherein said dynamically switchable capacitor is coupled in parallel with said flashlamp bulb.

9. The flashlamp control system of claim 7, wherein said digital control electronics identifies an uncharged state of said dynamically switchable capacitor and sends a switch signal to said isolation switch for electrically switching said isolation switch thereby isolating said dynamically switchable capacitor during the uncharged state of said dynamically switchable capacitor.

10. The flashlamp control system of claim 9, wherein when said at least one dynamically switchable capacitor is discharged, only charging cycle currents are switched to the isolated dynamically switchable capacitor.

11. The flashlamp control system of claim 10, further comprising:
a current sensing component electrically connected to said dynamically switchable capacitor for monitoring at least one of charge current and discharge current of said dynamically switchable capacitor, said current sensing component further electrically connected to said digital control electronics for sensing the monitored at least one of charge current and discharge current of said dynamically switchable capacitor.

12. The flashlamp control system of claim 1, further comprising:
a homogenizing element positioned proximate said flashlamp bulb for modifying said optical signal by decreasing the coefficient of variation of said optical signal both temporally and spectrally.

13. The flashlamp control system of claim 12, wherein said homogenizing element is selected from the group consisting of predetermined air gaps, diffusing homogenizing elements, imaging elements, non-imaging elements and light pipe homogenizing elements.

14. The flashlamp control system of claim 12, wherein the coefficient of variation of said modified optical signal is 0.25% or less and the coefficient of variation between each output is 10% or less.

15. The flashlamp control system of claim 1, further comprising:
- a spectral flattening filter positioned proximate said flashlamp bulb for modifying said optical signal by decreasing the spectral intensity variation of said optical signal;
- a spectral mask for masking first wavelength values in a first spectra obtained at a first predetermined flash multiplier or energy; and
- a spectral splicer for combining said first spectra with said masked first wavelength values with a second spectra obtained at a second predetermined flash multiplier or energy using said spectral mask to construct a high dynamic range spectral signal.

16. A method of controlling a flashlamp bulb employing digital control electronics, comprising:
- dynamically changing a drive frequency and duty cycle of a high voltage power supply as a charge voltage of a capacitor, electrically connected between said high voltage power supply and said flashlamp bulb, approaches a designated discharge voltage of said capacitor within less than a kilovolt difference between said charge voltage and said designated discharge voltage;
- generating a plurality of current pulses at said high voltage power supply by said digital control electronics based on said power supply drive frequency and duty cycle; and
- charging said capacitor employing said plurality of current pulses from said high voltage power supply.

17. The method of claim 16 further comprising controlling, by said digital control electronics, a recharge rate, an energy level setting and multiple pulsing of said flashlamp bulb.

* * * * *